(12) United States Patent
Yabsley

(10) Patent No.: US 10,897,933 B2
(45) Date of Patent: Jan. 26, 2021

(54) GARMENT WITH ABSORBENT PAD

(71) Applicant: Kelly Yabsley, Taylors, SC (US)

(72) Inventor: Kelly Yabsley, Taylors, SC (US)

( * ) Notice: Subject to any disclaimer, the term of this patent is extended or adjusted under 35 U.S.C. 154(b) by 0 days.

(21) Appl. No.: 16/379,247

(22) Filed: Apr. 9, 2019

(65) Prior Publication Data
US 2019/0254357 A1  Aug. 22, 2019

Related U.S. Application Data

(60) Provisional application No. 62/718,058, filed on Aug. 13, 2018.

(51) Int. Cl.
*A41B 13/08* (2006.01)
*A61F 13/15* (2006.01)

(52) U.S. Cl.
CPC ........ *A41B 13/08* (2013.01); *A41B 2300/324* (2013.01); *A41B 2400/60* (2013.01); *A61F 13/15* (2013.01)

(58) Field of Classification Search
CPC ..... A41B 10/00; A41B 2400/60; A41D 11/00; A61F 13/15
USPC .................................... 2/46, 80, 83, 69, 111
See application file for complete search history.

(56) References Cited

U.S. PATENT DOCUMENTS

| 2,671,220 A * | 3/1954 | Geissmann ............ A41B 13/00 2/80 |
| 4,548,604 A | 10/1985 | Ellsworth |
| 4,585,448 A | 4/1986 | Enloe |
| 4,753,647 A | 6/1988 | Curtis |
| 2004/0127880 A1 | 7/2004 | Weber |
| 2010/0011477 A1 * | 1/2010 | Lee ........................ A41D 27/12 2/46 |
| 2011/0245791 A1 * | 10/2011 | Miller ..................... A61F 13/84 604/385.01 |

* cited by examiner

*Primary Examiner* — Katherine M Moran
(74) *Attorney, Agent, or Firm* — Boudwin Intellectual Property; Daniel Boudwin

(57) ABSTRACT

A garment with absorbent pad. The garment includes a flexible body having an upper end and a lower end, wherein the flexible body can move between an open position and a closed position, such that opposing lateral sides of the flexible body are removably secured together via a first fastener. A head opening is disposed centrally along the upper end, and a pair of arm openings are disposed through the flexible body. A pair of leg openings are disposed on the lower end. An absorbent pad is disposed centrally on an interior surface of the flexible body, such that the absorbent pad can absorb fluid waste to protect the flexible body.

17 Claims, 3 Drawing Sheets

GARMENT WITH ABSORBENT PAD

CROSS REFERENCE TO RELATED APPLICATIONS

This application claims the benefit of U.S. Provisional Application No. 62/718,058 filed on Aug. 13, 2018. The above identified patent application is herein incorporated by reference in its entirety to provide continuity of disclosure.

BACKGROUND OF THE INVENTION

The present invention relates to garments with absorbent pads. More particularly, the present invention pertains to easily removable child garments having an absorbent pad to absorb excess waste material exiting from a child's diaper.

Many infants have explosive bowel movements exceeding the capacity of standard diapers. This often results in waste leaking from or otherwise exiting the diaper to soil the infant and their clothing, forcing parents to clean the infant, clothing, and any surrounding areas soiled by such an event. Many parents, when faced with the excessive cleanup required in these situations choose to simply discard the soiled clothing, requiring greater expense in replacing the garment. Additionally, many infant clothes are designed to be removed similar to traditional shirts, thereby spreading the waste across the infant as the clothing is removed. Therefore, a garment that parents can easily remove from an infant, having an absorbent pad that can minimize cleaning efforts required is desired.

In light of the devices disclosed in the known art, it is submitted that the present invention substantially diverges in design elements from the known art and consequently it is clear that there is a need in the art for an improvement to existing garments with absorbent pads. In this regard, the instant invention substantially fulfills these needs.

SUMMARY OF THE INVENTION

In view of the foregoing disadvantages inherent in the known types of garments with absorbent pads now present in the known art, the present invention provides a garment with absorbent pad wherein the same can be utilized for providing convenience for the user when removing the garment from the infant and minimizing cleanup required.

The present system comprises a flexible body having an upper end and a lower end, wherein the flexible body is configured to selectively move between an open position and a closed position, wherein the closed position, opposing lateral sides of the flexible body are removably secured together via a first fastener. A head opening is disposed centrally along the upper end and a pair of arm openings are disposed through the flexible body. A pair of leg openings are disposed on the lower end, and an absorbent pad is disposed centrally along an interior surface of the flexible body. In some embodiments, a flap extends from the lower end, wherein the flap is configured to removably secure to an exterior surface of the flexible body via a second fastener. In another embodiment, the absorbent pad is removably securable to the flexible body. In other embodiments, the absorbent pad further comprises an adhesive disposed across a rear surface thereof. In yet another embodiment, the absorbent pad further comprises a backing removably secured to the rear surface. In some embodiments, the absorbent pad further comprises a plurality of layers of quilted material. In another embodiment, a pair of arcuate cutouts are disposed along the lower end, wherein the pair of arcuate cutouts define the pair of leg openings when the flexible body is in the closed position. In other embodiments the first fastener extends along an entirety of each of the opposing lateral sides from the upper end to the lower end. In yet another embodiment, the pair of arm openings taper from an upper side thereof towards a lower side thereof. In some embodiments, the first fastener is disposed perpendicularly to the second fastener when the flexible body is in the closed position. In another embodiment, the absorbent pad further comprises a protrusion configured to extend along and contour with the flap.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
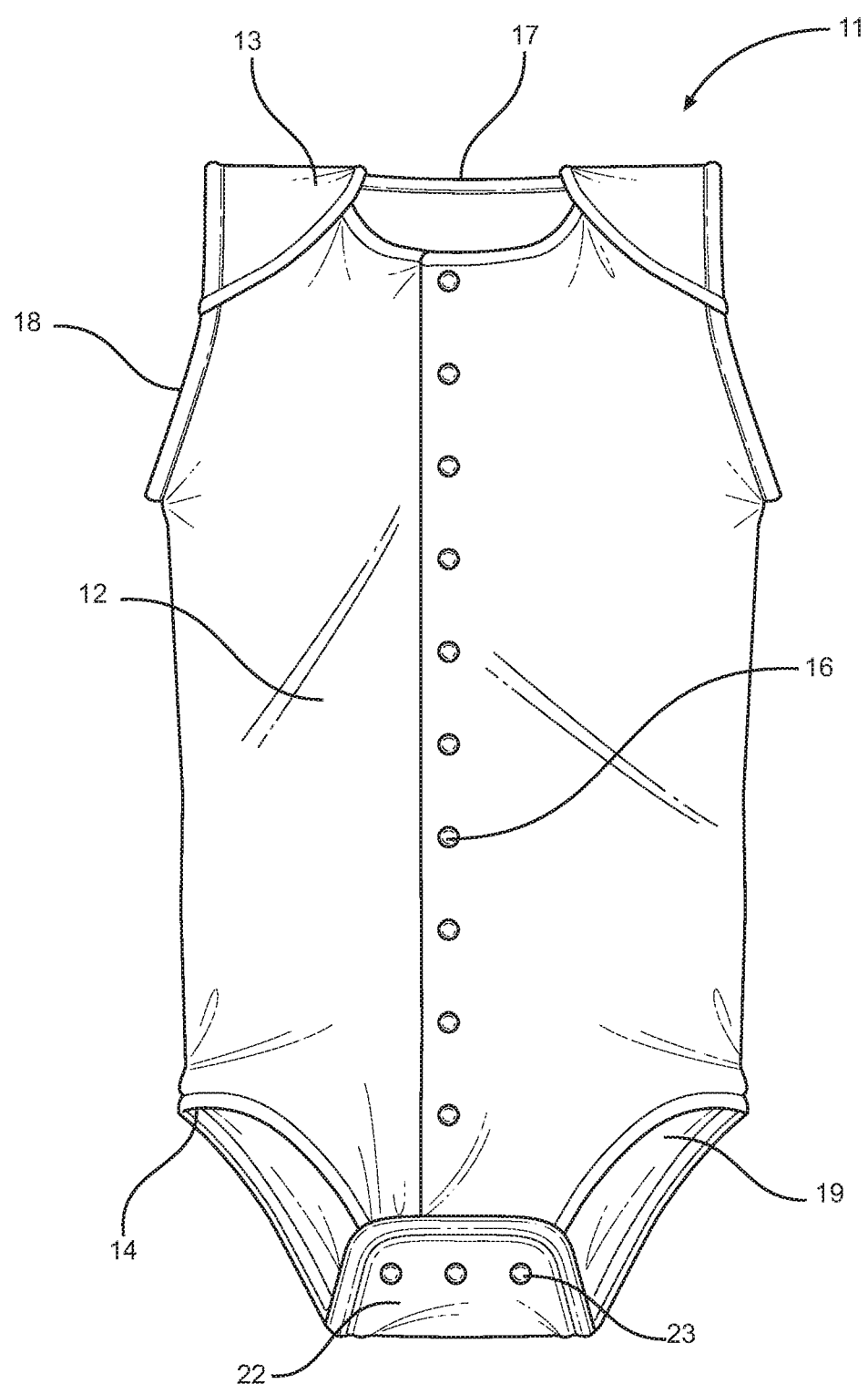
FIG. 1 shows a perspective view of an embodiment of the garment with absorbent pad in a closed position.

Reference is made herein to the attached drawings. Like reference numerals are used throughout the drawings to depict like or similar elements of the garment with absorbent pad. The figures are intended for representative purposes only and should not be considered to be limiting in any respect.

Referring now to FIG. 1, there is shown a perspective view of an embodiment of the garment with absorbent pad in a closed position. The garment 11 comprises a flexible body 12 having an upper end 13 and a lower end 14. In the illustrated embodiment, the upper end 13 and the lower end 14 further comprise a border comprising a greater thickness than the flexible body 12, such that the upper and lower ends 13, 14 provide increased comfort and reduce chafing to the infant. The flexible body 12 is configured to move between an open position and a closed position, wherein the closed position, the garment 11 is configured to encircle an infant's torso. A head opening 17 is disposed centrally along the upper end 13, wherein the head opening 17 is configured to receive a head of the infant therethrough when the flexible body 12 is in the closed position. Furthermore, a pair of arm openings 18 extend through the flexible body 12, such that the pair of arm openings 18 are each configured to receive an arm of the infant therethrough. Additionally, a pair of leg openings 19 are disposed along the lower end 14, wherein the pair of leg openings 19 are configured to receive a leg of the infant therethrough.

Figure 2:
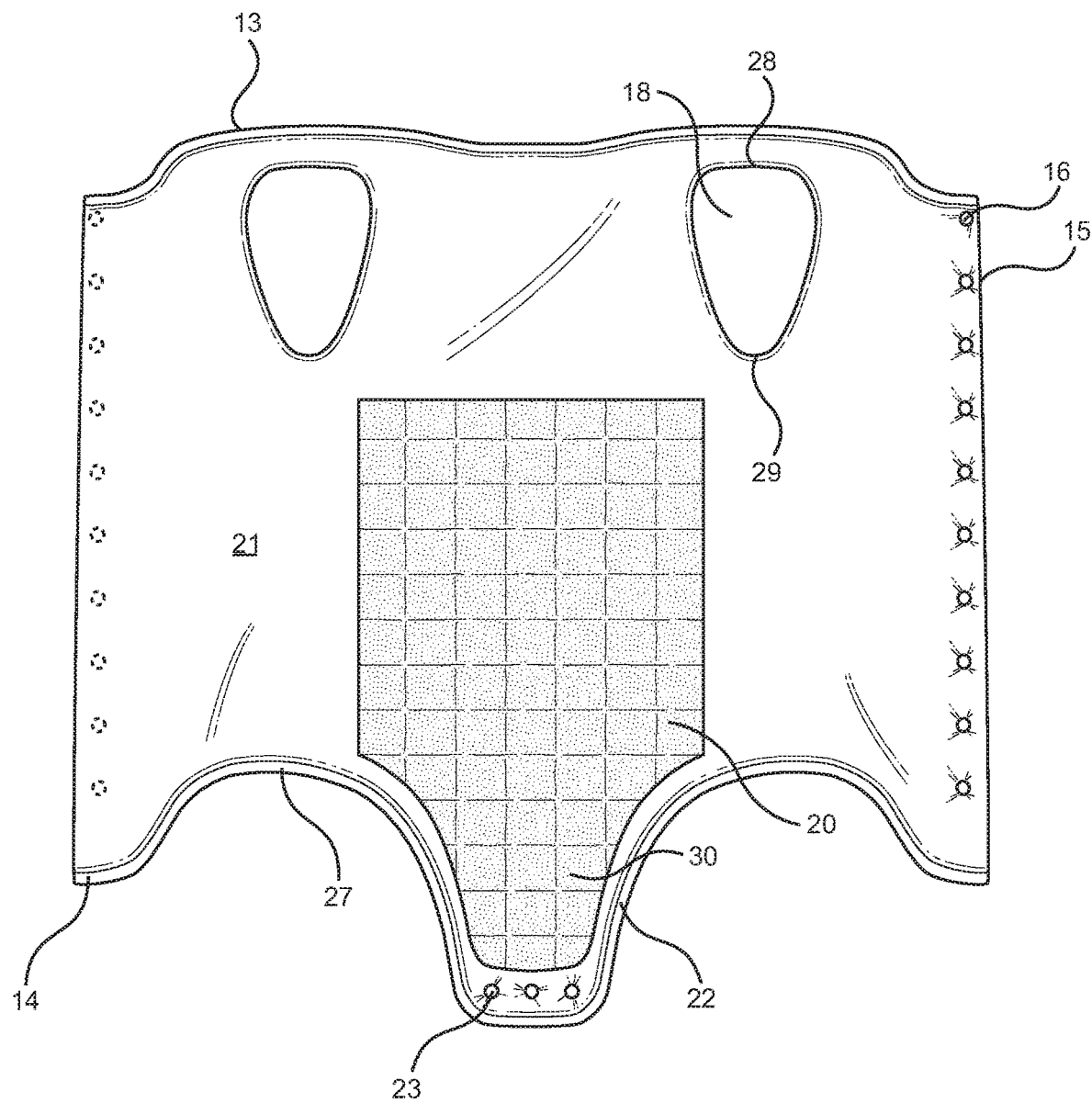
FIG. 2 shows a top plan view of an embodiment of the garment with absorbent pad in an open position.

In the illustrated embodiment the flexible body 12 is configured to fold over an infant along the front of the infant's torso, such that opposing lateral sides (as shown in FIG. 2, 15) are secured together via a first fastener 16. Furthermore, in the illustrated embodiment, the flexible body 12 further comprises a flap 22 extending from the lower end 14, wherein the flap 22 is configured to secure to an exterior surface of the flexible body 12 between each leg of the infant via a second fastener 23. In this way, the garment 11 is easily removable from the infant, allowing quick access to a soiled diaper for changing purposes. In the illustrated embodiment, the first and second fasteners 16, 23 are shown as snap fasteners disposed at regular intervals along the opposing lateral sides and the flap 22, respectively. However, in other embodiments, alternate quick-release fastening methods are contemplated, including hook and loop fasteners, buttons, and the like. Additionally, in the illustrated embodiment, the first and second fasteners 16, 23 are positioned perpendicularly relative to each other, such that the user can easily disengage each set of fasteners 16, 23 independently.

Referring now to FIG. 2, there is shown top plan view of an embodiment of the garment with absorbent pad in an open position. The first fastener 16 extends along the opposing lateral sides 15 of the flexible body, such that the opposing lateral sides 15 secure along a central line of the torso of the infant, allowing quick and efficient removal of the garment. In the illustrated embodiment, the first fastener 16 extends along an entirety of the opposing lateral sides 15 from the upper end 13 to the lower end 14, such that the garment remains secured around the infant during active movement. In some embodiments, the first fastener 16 comprises a plurality of individual fasteners disposed at regular intervals along the opposing lateral sides 15.

The pair of arm openings 18 are disposed through the flexible body, wherein the pair of arm openings 18 are each positioned to receive an arm of the infant therethrough when the garment is in the closed position. In the illustrated embodiment, the pair of arm openings 18 taper from an upper side 28 thereof towards a lower side 29 thereof. In this way, the pair of arm openings 18 are configured to provide increased comfort to the infant, while allowing the arms to have a full range of movement. Furthermore, in the illustrated embodiment, a pair of arcuate cutouts 27 are disposed along the lower end 14, wherein the pair of arcuate cutouts 27 define the pair of leg openings when the garment is in the closed position. The arcuate shape of the pair of arcuate cutouts 27 allows the pair of leg openings to define a substantially rounded shape, thereby increasing comfort and reducing chafing risks to the infant when the garment is worn.

In the illustrated embodiment, the flap 22 extends from the lower end 14 between the pair of arcuate cutouts 27. The flap 22 is configured to secure to the exterior surface of the flexible body when in the closed position via the second fastener 23, thereby securing the garment to the infant. The flap 22 further provides additional support to the diaper areas, allowing additional protections to the surrounding area should the diaper leak. In this way, the flap 22 is configured to capture leakage from the diaper. In the illustrated embodiment, the flap 22 further comprises a border along a perimeter thereof, continuous with the lower end 14, thereby forming a barrier configured to further decrease the risk of leakage escaping the garment.

An absorbent pad 20 is disposed centrally along an interior surface 21 of the flexible body. The absorbent pad 20 is configured to absorb and retain waste that leaks from a diaper worn by the infant. As such, the absorbent pad 20 is positioned to fully encompass a rear of a diaper worn under the garment, such that the any waste leaking from the diaper is captured thereby. In this way, the absorbent pad 20 prevents soiling of the garment, thereby minimizing the frequency of required cleaning. In the illustrated embodiment, the absorbent pad 20 comprises a protrusion 30 extending along the interior surface 21 and onto the flap 22. The protrusion 30 is configured to contour with the shape of the flap 22, ensuring that any waste leakage from the diaper adjacent to the flap 22 is captured by the protrusion 30. In this way, the protrusion 30 is configured to prevent soiling of the flap 22, allowing the absorbent pad 20 to fully encompass the rear of the diaper where leaks are most likely to occur.

Figure 3:
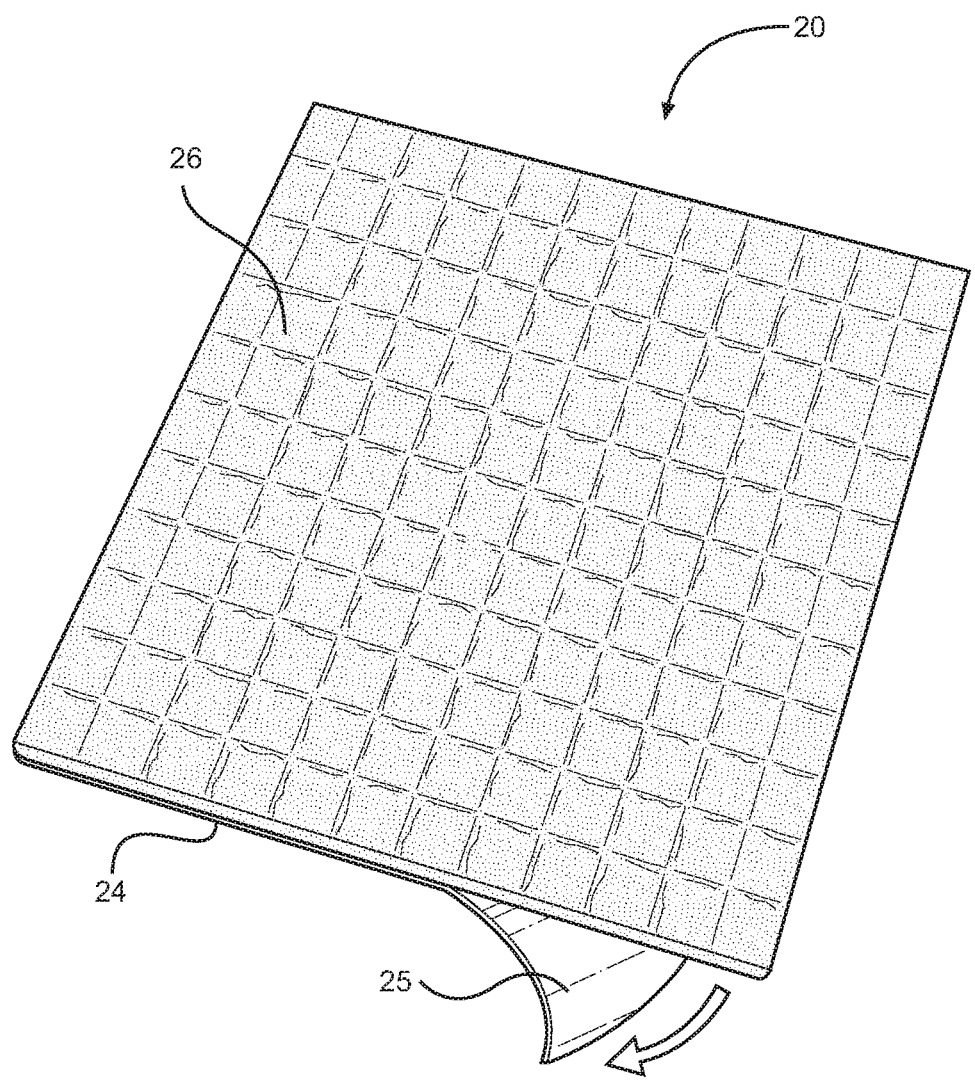
FIG. 3 shows a perspective view of the absorbent pad of an embodiment of the garment with absorbent pad.

Referring now to FIG. 3, there is shown a perspective view of the absorbent pad of an embodiment of the garment with absorbent pad. In the illustrated embodiment, the absorbent pad 20 comprises an alternate embodiment that lacks the protrusion. In this way, the user can more readily place the absorbent pad 20 along the interior surface of the flexible body as desired, ensuring that the garment is best protected from any waste leakage from the diaper. A front surface 26 of the absorbent pad 20 comprises an absorbent material configured to absorb and capture fluid waste leakage. In the illustrated embodiment, the front surface 26 comprises a plurality of layers of absorbent material, increasing the volume of fluid that can be absorbed by the absorbent pad 20. Furthermore, in the illustrated embodiment, the front surface 26 comprises a quilted pattern configured to increase surface area available for absorption, thereby allowing the absorbent pad 20 to wick fluid more quickly and efficiently.

In some embodiments, the absorbent pad 20 is removably securable to the garment, such that a user can easily dispose of the soiled absorbent pad 20 and replace the soiled absorbent pad 20 with an unsoiled absorbent pad 20. In the illustrated embodiment, a rear surface 24 of the absorbent pad 20 comprises an adhesive thereon, the adhesive configured to removably secure the absorbent pad 20 to the garment. Further, in the illustrated embodiment, the absorbent pad 20 further comprises a backing 25 removably securable to the rear surface 24, the backing 25 configured to prolong the efficacy of the adhesive until the user wishes to secure the absorbent pad 20 to the garment. In one exemplary use, the backing 25 is removed from the rear surface 24 and the absorbent pad 20 is positioned along the interior surface of the garment in a desired location to maximize waste leakage protection. The absorbent pad 20 is then secured to the garment via the adhesive. An infant is then secured within the garment such that the diaper overlaps the area protected by the absorbent pad 20, thereby ensuring that waste leakage from the diaper is captured thereby.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A garment with absorbent pad, comprising:
   a flexible body having an upper end and a lower end, wherein the flexible body is configured to selectively move between an open position and a closed position;
   wherein the closed position, opposing lateral sides of the flexible body are removably secured together via a first fastener;
   a flap extending from the lower end, wherein the flap is configured to removably secure to an exterior surface of the flexible body via a second fastener;
   a head opening disposed centrally along the upper end;
   a pair of arm openings disposed through the flexible body;
   a pair of leg openings defined by a pair of arcuate cutouts disposed on the lower end, wherein each of the pair of arcuate cutouts is disposed between one of the opposing lateral sides and the flap;
   an absorbent pad disposed centrally on an interior surface of the flexible body.

2. The garment with absorbent pad of claim 1, wherein the absorbent pad is removably securable to the flexible body.

3. The garment with absorbent pad of claim 2, wherein the absorbent pad further comprises an adhesive disposed across a rear surface thereof.

4. The garment with absorbent pad of claim 3, further comprising a backing removably secured to the rear surface of the absorbent pad.

5. The garment with absorbent pad of claim 1, wherein the absorbent pad further comprises a plurality of layers of quilted material.

6. The garment with absorbent pad of claim 1, wherein the first fastener extends along an entirety of each of the opposing lateral sides from the upper end to the lower end.

7. The garment with absorbent pad of claim 1, wherein the pair of arm openings taper from an upper side thereof towards a lower side thereof, such that the upper side comprises a greater width than that of the lower side.

8. The garment with absorbent pad of claim 1, wherein the first fastener is disposed perpendicularly to the second fastener when the flexible body is in the closed position.

9. The garment with absorbent pad of claim 1, wherein the absorbent pad further comprises a protrusion dimensioned to contour with a perimeter of the flap.

10. The garment with absorbent pad of claim 1, wherein the upper end and the lower end each include a border having a thickness greater than a thickness of the flexible body.

11. The garment with absorbent pad of claim 10, wherein the border extends along an entirety of each of the upper end and the lower end.

12. The garment with absorbent pad of claim 10, wherein the border along the lower end extends along the perimeter of the flap.

13. The garment with absorbent pad of claim 1, wherein the entirety of the absorbent pad comprises an absorbent material.

14. The garment with absorbent pad of claim 1, wherein the second fastener is disposed between the pair of leg openings when in the closed position.

15. The garment with absorbent pad of claim 1, wherein the second fastener comprises a plurality of fasteners disposed in a linear arrangement along a distal end of the flap, wherein the plurality of fasteners removably secure to complementary fasteners disposed on an exterior side of the flexible body.

16. The garment with absorbent pad of claim 15, wherein the complementary fasteners are disposed on an exterior surface of a portion of the lower end defined between the opposing lateral sides and the pair of arcuate cutouts.

17. A garment with absorbent pad, consisting of:
   a flexible body having an upper end and a lower end, wherein the flexible body is configured to selectively move between an open position and a closed position;
   wherein in the closed position, opposing lateral sides of the flexible body are removably secured together via a first fastener;
   a flap extending from the lower end, wherein the flap is configured to removably secure to an exterior surface of the flexible body via a second fastener;
   a head opening disposed centrally along the upper end;
   a pair of arm openings disposed through the flexible body;
   a pair of leg openings defined by a pair of arcuate cutouts disposed on the lower end, wherein each of the pair of arcuate cutouts is disposed between one of the opposing lateral sides and the flap;
   an absorbent pad disposed centrally on an interior surface of the flexible body.

\* \* \* \* \*